(12) United States Patent
Morgan

(10) Patent No.: US 7,389,148 B1
(45) Date of Patent: Jun. 17, 2008

(54) ELECTRODE DESIGN FOR DEFIBRILLATION AND/OR SENSING CAPABILITIES

(75) Inventor: Kevin L. Morgan, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 543 days.

(21) Appl. No.: 10/840,528

(22) Filed: May 5, 2004

(51) Int. Cl.
*A61N 1/05* (2006.01)
(52) U.S. Cl. ............... 607/116; 600/372; 600/373; 600/374
(58) Field of Classification Search ......... 607/116; 600/372–374
See application file for complete search history.

(56) References Cited

U.S. PATENT DOCUMENTS

| 4,280,511 | A |   | 7/1981  | O'Neill .............. 128/784 |
| 5,458,629 | A |   | 10/1995 | Baudino et al. ........ 607/116 |
| 5,477,856 | A | * | 12/1995 | Lundquist ............ 600/373 |
| 5,524,619 | A | * | 6/1996  | Ouchi et al. ........... 600/393 |
| 5,730,127 | A | * | 3/1998  | Avitall ............... 600/374 |
| 6,090,104 | A | * | 7/2000  | Webster, Jr. .......... 606/41 |
| 6,216,045 | B1 |  | 4/2001  | Black et al. .......... 607/122 |
| 6,273,876 | B1 | * | 8/2001  | Klima et al. .......... 604/264 |
| 6,356,790 | B1 | * | 3/2002  | Maguire et al. ........ 607/102 |
| 6,493,590 | B1 |  | 12/2002 | Wessman et al. ........ 607/116 |
| 6,604,003 | B2 | * | 8/2003  | Fredricks et al. ....... 607/99 |
| 6,685,679 | B2 | * | 2/2004  | Merdan ............... 604/264 |
| 6,921,397 | B2 | * | 7/2005  | Corcoran et al. ........ 604/535 |
| 2004/0254450 | A1 | * | 12/2004 | Griffin et al. ........ 600/411 |

FOREIGN PATENT DOCUMENTS

| WO | WO 95/22371 | 8/1995 |
| WO | WO 00/64530 | 11/2000 |

OTHER PUBLICATIONS de Chazal; Philip, Member IEEE, et al., "Automated Processing of the Single-Lead Electrocardiogram for the Detection of Obstructive Sleep Apnoea," *IEEE Trans. Biomedical Eng.*; vol. 50, No. 6 (2003), pp. 686-696.
Worley, Seth J. et al. "Optimization of Cardiac Resynchronization: Left Atrial Electrograms Measured at Implant Eliminates the Need for Echo and Identified Patients Where AV Optimization is not Possible," *Journal of Cardiac Failure*, vol. 10, No. 4 Suppl. (2004).

* cited by examiner

*Primary Examiner*—Carl Layno
*Assistant Examiner*—Yun Haeng Lee

(57) ABSTRACT

A ring electrode for an implantable medical device includes a conductive tubular member adapted to be attached to a lead body and having a continuous generally helical slot formed therein to form a coil thereby enabling omni directional bending. The coil is of flattened cross section and in one embodiment, the coil is shaped as a spiral of uniform pitch. In another embodiment, a plurality of uniformly spaced dovetail joints connect a plurality of first and second adjacent loops. Each dovetail joint includes a plurality of uniformly spaced wedge-shaped tenons projecting longitudinally from a first loop, a plurality of uniformly spaced wedge-shaped mortises longitudinally indented into a second loop, the wedge-shaped mortises being similarly shaped and sized in relation to the wedge-shaped tenons, the plurality of wedge-shaped tenons being fittingly received by the wedge-shaped mortises at all locations between the proximal and distal ends of the ring electrode.

5 Claims, 3 Drawing Sheets

ELECTRODE DESIGN FOR DEFIBRILLATION AND/OR SENSING CAPABILITIES

FIELD OF THE INVENTION

The present invention relates generally to leads used in sensing electrical activity within a patient and administering therapy, and more particularly to such leads incorporating band electrodes configured for improved flexibility and tractability within the body.

BACKGROUND

A variety of medical electrode leads are available today for the diagnosis and treatment of various disorders of the cardiovascular and neurological systems. These electrode leads can be used to sense electrical activity within the body and to deliver different forms of energy to stimulate, ablate, cauterize or pace. The core electrode technology common to all of these lead designs is the application of one or more metallic bands on a lead body. Examples of medical leads using metallic banded electrodes include permanent and temporary cardiac pacing leads, electro-physiologic (EP) leads, electrocautery probes and spinal stimulation leads. The use of pre-formed metallic band electrodes manufactured from noble metals, such as gold or platinum and various other conductive alloys has found widespread application despite their functional design and performance limitations.

Metallic band electrodes possess distinct steerability problems. The steerability problems arise from the inflexible nature of the circular rings or bands. These inflexible bands of metal are typically adhesively bonded, crimped or otherwise attached to the exterior surface of the lead body. The bands are electrically coupled to electrical conductors that typically extend through one or more lumens in the lead body. The bands tend to be relatively thick and are therefore rigid. For neurological applications, the bands are typically about 3 millimeters wide. When it is considered that often multiple ring electrodes are employed at spaced locations along the distal end portion of the lead body, they significantly impact the ability of the distal end portion of the lead to flex and conform to tissue structures.

As noted above, band electrodes placed on a flexible lead stiffen the lead and thereby reduce its steerability. As such, leads having band electrodes are often restricted to applications where steerability and selective placement are not required and affect a variety of applications.

In cardiac therapies, such as for example ablation therapy, precise steerability and placement of a lead is necessary. Ablation therapy requires that a lead having sensing/ablation electrodes on the distal end is steered through the patient's vascular system and into a predetermined chamber of the heart. The lead is manipulated so as to place the electrodes into direct contact with the myocardial tissue that is sensed and/or to be ablated. The aberrant path and/or ectopic foci is first located using a mapping technique in which cardiac depolarization signals picked up by the electrodes are transmitted over electrical conductors in the lead to a suitable monitor/analyzer. Once located, the aberrant conductive pathway or the ectopic foci is ablated. This procedure requires the ability to precisely control the lead over the surfaces of the heart. Therefore, a need exists for a lead that provides precise control and steerability to accurately locate the electrodes in the heart.

The process of terminating an arrhythmia such as ventricular fibrillation is accomplished by means of a high energy shock to the myocardium. When using defibrillation leads placed inside the heart (endocardially), the most accepted method to deliver the shock is through a helical wound coil electrodes placed inside the heart.

The method of using helical wound coils to terminating atrial or ventricular fibrillation is satisfactory in principle. Coils do however have large gaps and spaces between the windings which encourage fibrotic growth to intertwine. This effectively locks the lead into the myocardial tissue. The lead then becomes extremely difficult if not impossible to remove without invasive surgery. Furthermore, coil electrodes can stretch, unwind, expand, or contract. This can give the implanting physician an unreliable sense of feel when implanting the lead. The lead can also build up a torque load (similar to winding up a spring) if the lead is twist or turned.

Another disadvantage to coil windings is that the coils are positioned on the outer lead body. This increases the overall diameter of the lead significantly. Furthermore, the coil windings result in a stiffer lead since the coils restrict the bending of the lead.

There is a problem regarding low voltage bradycardia ring electrodes. Traditionally, ring electrodes for low voltage applications use a solid tube (or ring) for creating the electrode. Historically, this design has been utilized for all low voltage applications. However, it can become difficult when placing LV leads with ring electrodes in the left side of the heart via the coronary sinus. The ring electrodes are a hindrance because of the stiffness they incur on the lead. Since the ring is a solid tube of metal, the lead stiffens in the region of the ring. This stiffness makes the lead very difficult if not impossible to place in the left side of the heart through the coronary sinus.

Also, an RV or RA ring electrode can hinder placement of a lead by creating a stiff section which can create drag or jamming in an introducer sheath or within the vein when implanting the lead.

A number of patents typify the prior art in regard to lead constructions for cardiac pacing, for example, intended to be placed in the chambers of the heart or the coronary venous system and thereby subjected to a series of tortuous bends, the leads having the flexibility to follow these bends but having enough structural support to allow them to be pushed and twisted in order to navigate within these veins.

In this regard, U.S. Pat. No. 4,280,511 to O'Neill discloses a ring electrode for a pacing lead in which the electrode is secured to a conductor coil by soft metal disposed in a slit in insulation covering the conductor coil. U.S. Pat. No. 5,458,629 to Baudino et al. discloses a lead in which ring electrodes are constructed according to a novel technique in which the body of the lead is etched or milled to provide notches and the ring electrodes are formed by enplacing a C-shaped conductor over the notch and closing it into place to provide an isodiametric lead construction. U.S. Pat. No. 6,493,590 to Wessman et al. discloses a lead construction provided for use in stimulating body tissue or an organ that has a flexible band electrode including at least one slot configured to provide increased flexibility.

SUMMARY

An electrode for an implantable medical device includes a conductive tubular member adapted to be attached to a lead body and having a continuous generally helical slot formed therein to form a coil thereby enabling omni directional bending. The coil is of flattened cross section and in one embodiment, the coil is shaped as a spiral of uniform pitch. In another embodiment, a plurality of uniformly spaced dovetail joints connect a plurality of first and second adjacent loops. Each dovetail joint includes a plurality of uniformly spaced wedge-shaped tenons projecting longitudinally from a first loop, a plurality of uniformly spaced wedge-shaped mortises longitudinally indented into a second loop, the wedge-shaped mortises being similarly shaped and sized in relation to the wedge-shaped tenons, the plurality of wedge-shaped tenons being fittingly received by the wedge-shaped mortises at all locations between the proximal and distal ends of the ring electrode.

In another embodiment, an electrode is described that is capable of shocking or sensing within the heart. The electrode is comprised of a metallic tube suitable for an electrode such as platinum. This tube has a continuous pattern cut into it to provide flexibility to the tube, the cut being typically made by use of a laser beam. The cuts made into the tubing can be of any pattern that provides the desired flexibility.

The tube can be made thinner than a conventional coil winding used in a defibrillation electrode. This thinner wall construction will then provide thinner lead designs with improved flexibility. A lead formed in this manner will also be more isodiametric, that is, the diameter of the lead will be substantially uniform in size. This is desired when implanting the lead. With a smooth and uniform outer periphery, the lead is able to slide though an introducer without undesirably "hanging up" on an implant tool or on heart tissue.

This design is also advantageous if the lead ever needs to be removed. The electrode provides a smoother outer surface than a conventional coil electrode. This results in a reduced tendency for fibrotic ingrowth that might intertwine with the electrode. This results in a lead that can be removed much easier than conventional leads with less trauma to the heart.

This electrode can also be used as a low voltage "ring" electrode on bradycardia leads. A ring electrode that can be flexible has an advantage over a conventional ring electrode when placing a lead into the coronary sinus. This is realized when an implanting physician is navigating the coronary venous system. Bends, curves, and junctions of veins create a very difficult path for the lead to follow. A lead with a conventional ring electrode has a stiff area including the ring and the areas on either side of the ring. This stiff area reduces the ability of the lead to navigate the venous system. A flexible electrode greatly reduces the stiffness and gives a greater handling characteristic to the lead.

Other and further features, advantages, and benefits will become apparent in the following description taken in conjunction with the following drawings. It is to be understood that the foregoing general description and the following detailed description are exemplary and explanatory but are not to be restrictive of the invention. The accompanying drawings illustrate certain embodiments, and together with the description, serve to explain the illustrative embodiments in general terms. Like numerals refer to like parts throughout the disclosure.

BRIEF DESCRIPTION OF THE DRAWINGS

The foregoing aspects and other features are explained in the following description, taken in connection with the accompanying drawings, wherein.

DETAILED DESCRIPTION OF THE PREFERRED EMBODIMENT

Figure 1:
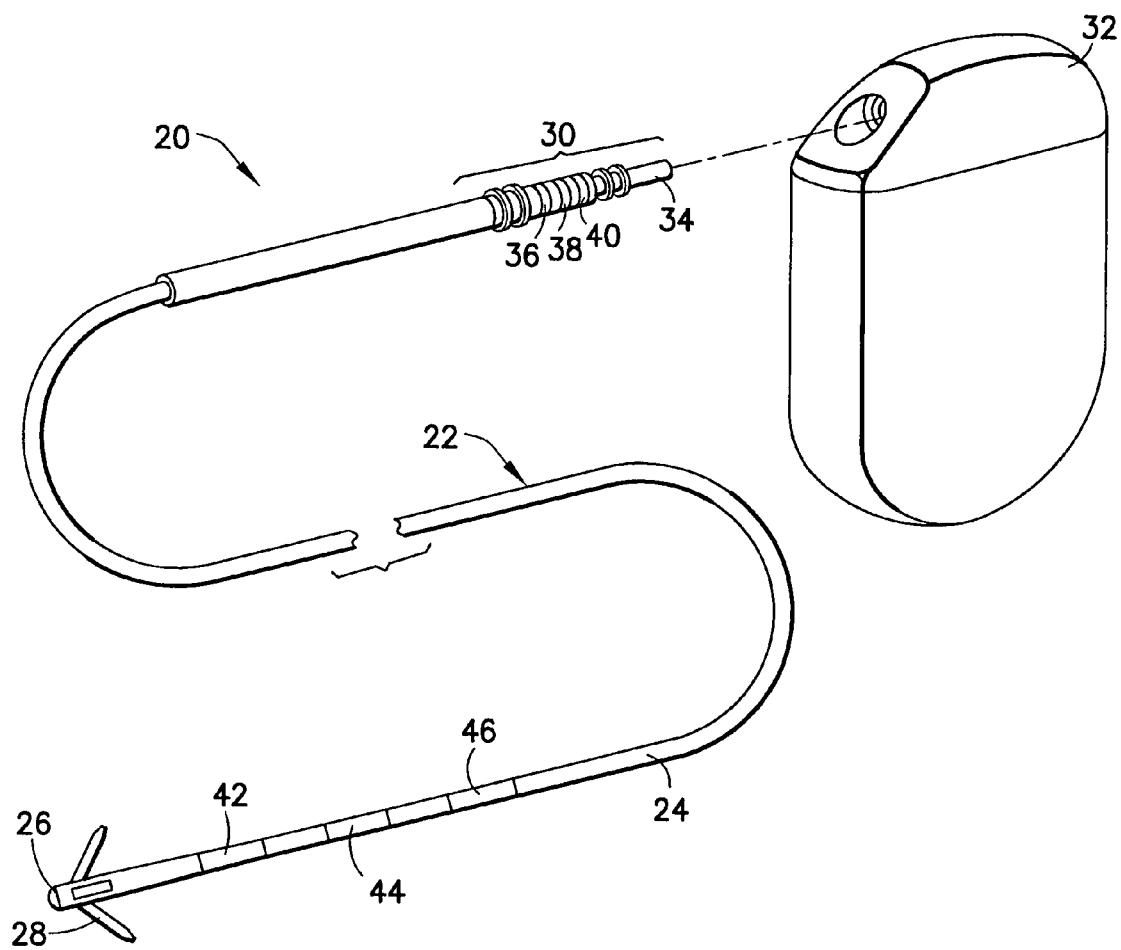
FIG. 1 is a is a perspective exploded view of a body implantable lead system according to one illustrative embodiment and positioned for engagement at one end with heart tissue and at the other end for insertion into a body stimulation device such as a pacemaker and/or defibrillator.

Turn now to the drawings and, initially to FIG. 1, which generally illustrates a body implantable lead system 20 of the endocardial type according to one illustrative embodiment. Although a number of embodiments are shown in the drawings, it should be understood that the present invention can be embodied in many alternate forms or embodiments. In addition, any suitable size, shape or type of elements or materials could be used.

The lead system 20 which is of a multi-polar design includes a lead body 22 with an insulating sheath 24 interconnecting a distal electrode 26 secured adjacent an interior wall of an organ such as the heart by means, for example, of fixing tines 28 which engage the tissue or trabeculae of the heart. The lead system 20 also includes an electrical connector 30 at a proximal end to which can be attached a source of electrical energy such as a pacemaker 32. In a known manner, connector pin terminal 34 is electrically in common with the cathode tip electrode 26 at the distal end of the lead and connector rings 36, 38, and 40 are electrically in common with electrodes 42, 44, and 46, respectively.

The insulating sheath 24 of the lead body 22 is composed of flexible biocompatible flexible polymeric insulating material such as silicone rubber, polyurethane, PTFE (polytetrafluoroethylene), or ETFE (ethyltetra fluoroethylene). In similar fashion, the material of the electrodes is typically platinum, gold, silver, platinum-iridium, stainless steel, MP35N, or alloys thereof.

Figure 2:
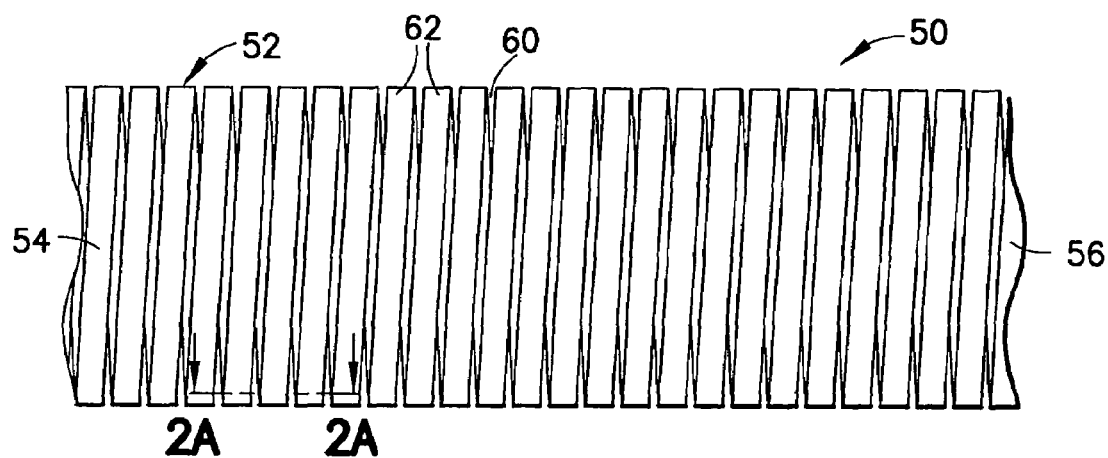
FIG. 2 is a detail elevation view of one embodiment of an electrode.
Figure 2A:
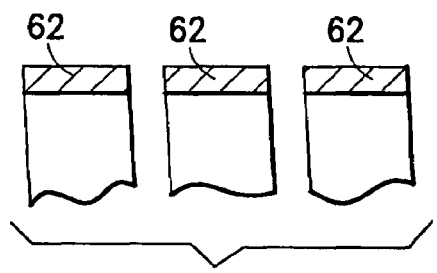
FIG. 2A is a cross section view taken generally along line 2A-2A in FIG. 2.
Figure 3:
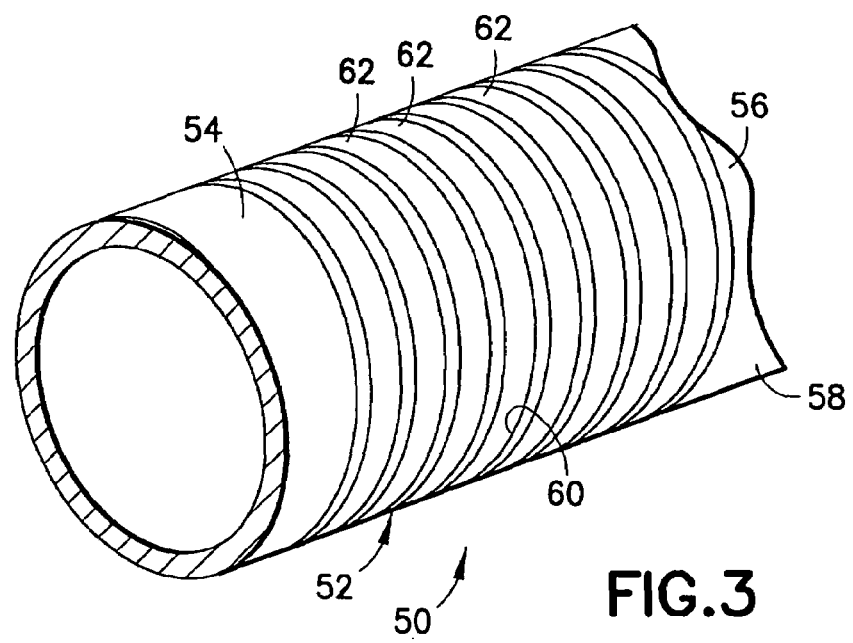
FIG. 3 is a detail perspective view of the electrode illustrated in FIG. 2.

Turn now to FIGS. 2 and 3 for one illustrative embodiment of a ring electrode 50, which is capable of omni directional bending. In this instance, a conductive tubular member 52 extends between proximal and distal ends 54, 56, respectively, and is adapted to be attached at its proximal and distal ends to a lead body 58 (FIG. 3). In this instance, a continuous generally helical slot 60 is formed, in effect, creating a coil 62 that extends between the proximal and distal ends of the tubular member 52. The resulting coil is in the shape of a spiral of uniform pitch and of flattened cross section as seen in FIG. 2A. However, it should be understood that the pitch, or even the width, of the coil 62 does not necessarily have to be constant.

Figure 4:
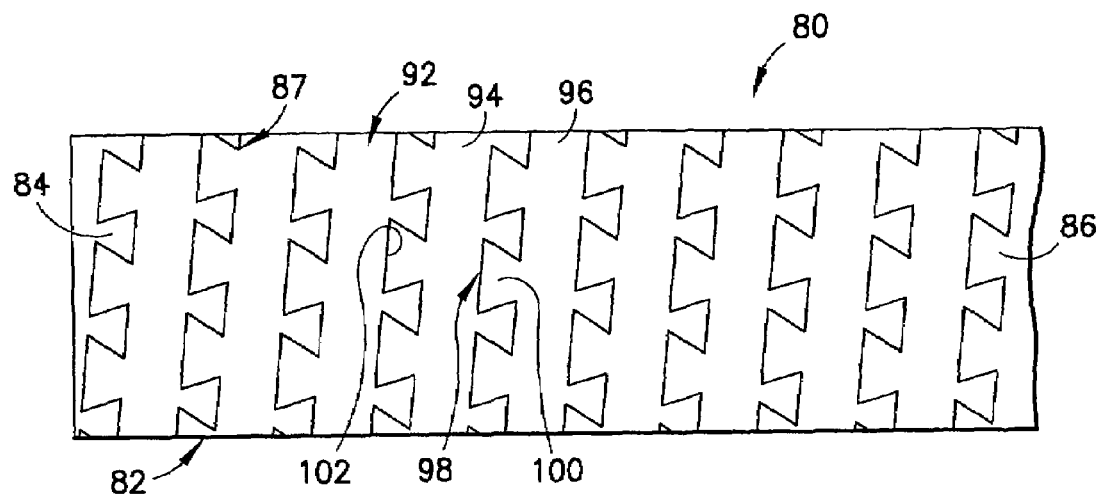
FIG. 4 is a detail elevation view of another embodiment of an electrode.
Figure 5:
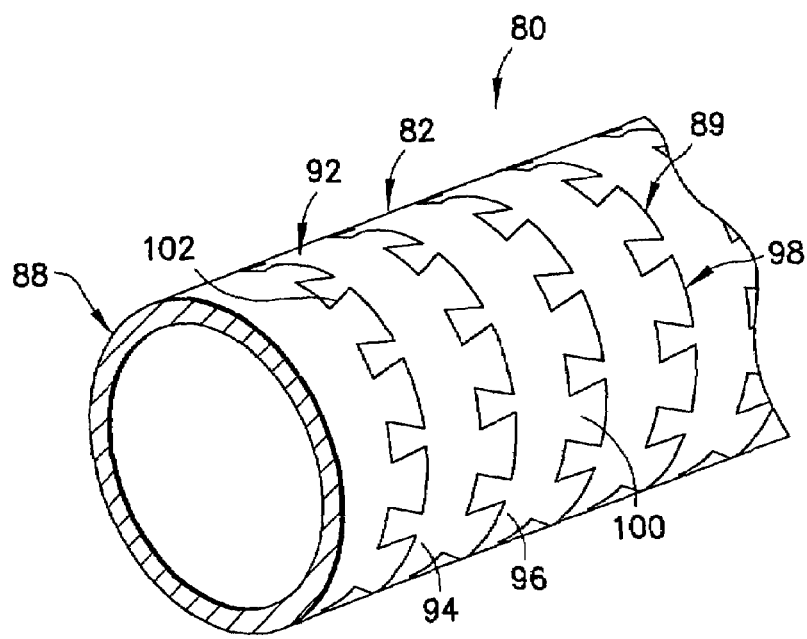
FIG. 5 is a detail perspective view of the electrode illustrated in FIG. 4.

Turn now to FIGS. 4 and 5 for another embodiment. In this instance, a ring electrode 80 includes a conductive tubular member 82 extending between proximal and distal ends, respectively, and is suitably attached at its proximal and distal ends to a lead body 88. The tubular member 82 may be scribed, as by a laser, to form a continuous generally helical slot 89 to form a coil 92 extending between the proximal and distal ends. The coil 92 has a plurality of first and second adjacent loops 94, 96 connected by a plurality of uniformly spaced dovetail joints 98. Each dovetail joint includes a plurality of uniformly spaced wedge-shaped tenons 100 projecting longitudinally from a first loop and a plurality of uniformly spaced wedge-shaped mortises 102 longitudinally indented into a second loop. The wedge-shaped mortises 102 are similarly shaped and sized in relation to the wedge-shaped tenons 100 and the wedge-shaped tenons are fittingly received by the wedge-shaped mortises at all locations between the proximal and distal ends of the resulting ring electrode 80.

Again, as in the instance of the embodiment depicted in FIGS. 2, 2A, and 3, the ring electrode 80 is capable of omni directional bending which makes it particularly desirable for traversing the tortuous route often required of a cardiac lead.

While ring electrode 80 is described as being scribed to form a continuous, generally helical slot 89, it will be apparent to those skilled in the art that other embodiments are also possible. For example, the ring electrode can be scribed to form a plurality of adjacent, generally annular shaped rings, each being formed with the tenons 100 on one circumferential edge and mortises 102 on the other edge to keep the annular shaped rings from separating.

It should be understood that the foregoing description is only illustrative of the various embodiments. Various alternatives and modifications can be devised by those skilled in the art without departing from the invention. Accordingly, the present invention is intended to embrace all such alternatives, modifications and variances which fall within the scope of the appended claims.

What is claimed is:

1. An electrode for an implantable lead, the electrode comprising:
   a conductive tubular member extending between proximal and distal ends and adapted to be attached at its proximal and distal ends to a lead body, the tubular member having a continuous generally helical slot formed therein to form a coil extending between the proximal and distal ends of the tubular member, wherein the coil has a plurality of first and second adjacent loops connected by a plurality of uniformly spaced dovetail joints;
   whereby the electrode is capable of omni directional bending.

2. A ring electrode as set forth in claim 1 wherein the coil is in the shape of a spiral of uniform pitch.

3. A ring electrode as set forth in claim 1 wherein the coil is of flattened cross section.

4. A ring electrode as set forth in claim 1 wherein each dovetail joint includes:
   a plurality of uniformly spaced wedge-shaped tenons projecting longitudinally from a first loop;
   a plurality of uniformly spaced wedge-shaped mortises longitudinally indented into a second loop, the wedge-shaped mortises being similarly shaped and sized in relation to the wedge-shaped tenons;
   the plurality of wedge-shaped tenons being fittingly received by the wedge-shaped mortises at all locations between the proximal and distal ends of the ring electrode.

5. A ring electrode as set forth in claim 1 wherein the conductive tubular member is of a material selected from the group consisting of platinum, gold, silver, platinum-iridium, stainless steel and MP35N.

* * * * *